(12) United States Patent
Scott

(10) Patent No.: US 7,785,281 B2
(45) Date of Patent: Aug. 31, 2010

(54) SHOULDER STABILIZER SYSTEM

(75) Inventor: John Scott, Dallas, TX (US)

(73) Assignee: New Options Sports, Dallas, TX (US)

( * ) Notice: Subject to any disclaimer, the term of this patent is extended or adjusted under 35 U.S.C. 154(b) by 156 days.

(21) Appl. No.: 12/020,679

(22) Filed: Jan. 28, 2008

(65) Prior Publication Data

US 2009/0149787 A1 Jun. 11, 2009

Related U.S. Application Data

(60) Provisional application No. 60/898,226, filed on Jan. 29, 2007.

(51) Int. Cl.
*A61F 5/00* (2006.01)
(52) U.S. Cl. .............................. 602/4; 602/5
(58) Field of Classification Search ................. 602/4–5, 602/19, 61–62; 128/869, 874–875
See application file for complete search history.

(56) References Cited

U.S. PATENT DOCUMENTS

| 4,735,198 A | * | 4/1988 | Sawa | 128/878 |
| 5,609,569 A | * | 3/1997 | Offenhartz | 602/61 |
| 5,628,725 A | * | 5/1997 | Ostergard | 602/62 |
| 6,106,493 A | * | 8/2000 | Rozell | 602/20 |
| 6,398,746 B2 | * | 6/2002 | Bramlage et al. | 602/5 |
| 7,081,101 B1 | * | 7/2006 | Sawa | 602/19 |

* cited by examiner

*Primary Examiner*—Michael A. Brown
(74) *Attorney, Agent, or Firm*—Winstead PC

(57) ABSTRACT

An orthopedic stabilization device for use on a shoulder of a wearer for shoulder stabilization includes a torso portion having a closed end side and an open end side, the torso portion adapted to be secured around an upper torso of the wearer, a sleeve disposed on the torso closed end side, the sleeve adapted to be secured around a shoulder and an upper arm of the wearer, and a first plurality of straps, connected at their proximal end to the sleeve, the first plurality of straps having a first plurality of fasteners disposed at their distal end. The orthopedic stabilization device further includes a second plurality of straps having a second plurality of fasteners disposed at each end, whereby customizable restriction of shoulder movement may be attained by securing the first and second plurality of straps to the torso portion at various positions.

20 Claims, 7 Drawing Sheets

GRADE I AND II A/C SEPARATION

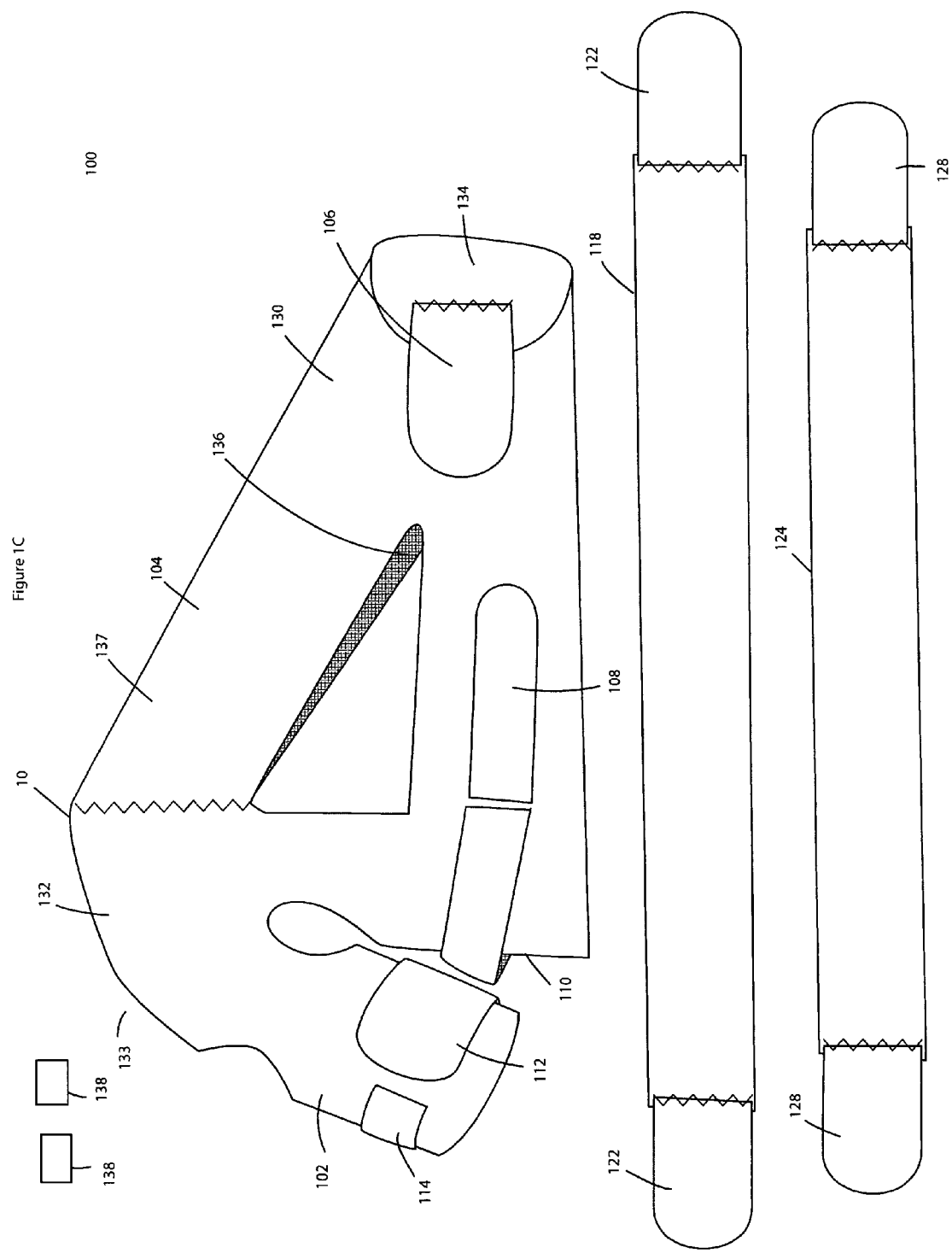

GRADE I AND II A/C SEPARATION

SHOULDER STABILIZER SYSTEM

CROSS REFERENCE TO RELATED APPLICATIONS

This application claims priority to, and incorporates by reference, U.S. Provisional Application 60/898,226, filed Jan. 29, 2007 entitled SHOULDER STABILIZER SYSTEM.

BACKGROUND OF THE INVENTION

1. Field of Invention

The present invention relates to the field of orthopedic braces and, more particularly, but not by way of limitation, to an adjustable shoulder stabilizer system for restricting bodily movement.

2. History of Related Art

Due to its bone structure and extensive range of possible movements, the shoulder is an intricate portion of a human body. The shoulder comprises three bones: a clavicle, a scapula, and a humerus. The three bones then form three joints: a glenohumeral joint, an acromioclavicular joint, and a sternoclavicular joint. Several major muscles attach to the scapula, the clavicle, or the humerus and are capable of controlling the movement of one or more of the joints. With a wide array of possibilities for movement of the shoulder, athletes and layusers alike frequently use these joints and are at risk for an even wider array of shoulder injuries. It has been reported by the American Academy of Orthopedic Surgeons that approximately four million people in the United States each year seek medical treatment for shoulder injuries such as sprains, strains, dislocations, and the like. When such an injury occurs, for example, with an acromioclavicular (AC) separation, standard treatment options include rest and non-use of the shoulder, which often involves placing the arm corresponding to the injured shoulder in a sling.

With the complexity of the shoulder, however, non-use is itself a problematic requirement. Shoulder stabilizers are frequently used to stabilize and restrict the shoulder from movement; however, those known in the art are typically limited to specified restrictions and injuries and therefore lack customizability, and lack the additional ability to function as a sling. Additionally, other injuries may be incurred along with a shoulder injury, including rib, biceps, and triceps injuries. These types of injuries may also require stabilization and immobilization. The prior art, however, does not allow for this level of flexibility and customization.

For the aforementioned reasons, there is a need in the art for a shoulder stabilizer that overcomes these limitations to provide a new level of flexibility and customizability.

SUMMARY OF THE INVENTION

The present invention relates to a shoulder stabilizer system for stabilizing and limiting the movement of specifically the shoulder, but also muscles within the arm and torso regions of the human body. More particularly, in one aspect of the present invention, various embodiments of the present invention include a customizable shoulder stabilization system. The system allows medical professionals and individuals to customize the shoulder stabilizer to an individual's particular injury. The placement and subsequent securing of a plurality of straps at any location on the shoulder stabilizer permits precision control as to which body movements will be limited.

An orthopedic stabilization device for use on a shoulder of a wearer for shoulder stabilization includes a torso portion having a closed end side and an open end side, the torso portion adapted to be secured around an upper torso of the wearer, a sleeve disposed on the torso closed end side, the sleeve adapted to be secured around a shoulder and an upper arm of the wearer, and a first plurality of straps, connected at their proximal end to the sleeve, the first plurality of straps having a first plurality of fasteners disposed at their distal end. The orthopedic stabilization device further includes a second plurality of straps having a second plurality of fasteners disposed at each end, whereby customizable restriction of shoulder movement may be attained by securing the first and second plurality of straps to the torso portion at various positions.

A method for stabilizing a shoulder of a wearer of the type used in an orthopedic treatment, the method includes providing a shoulder stabilization device having a sleeve and a torso portion adapted to receive an arm of the wearer, inserting the arm of the wearer through the sleeve of the shoulder stabilization device, and securing the torso portion around an upper torso of the wearer. The method further includes securing the torso portion around an upper torso of the wearer, adjusting a first plurality of straps to restrict lateral movement of the shoulder to a desired range, and selectively applying at least one strap of a second plurality of straps to further restrict the shoulder to a desired range of motion, whereby the selective application of the second plurality of straps allows customization of the shoulder stabilization device.

A method for stabilizing a shoulder of a wearer of the type used in an orthopedic treatment, the method includes providing a shoulder stabilization device having a sleeve and a torso portion adapted to receive an arm of the wearer, inserting the arm of the wearer through the sleeve, and securing the torso portion around an upper torso of the wearer. The method further includes securing the torso portion around an upper torso of the wearer, securing the sleeve around an upper arm and shoulder of the wearer, adjusting the plurality of straps attached to the sleeve to restrict lateral movement of the shoulder to a desired range, applying a first strap, having a fastener disposed at each end, so as to support a wrist and hand of the user and applying a second strap, having a fastener disposed at each end, so as to support an elbow and lower arm of the user, whereby the application of the first and second straps enables the shoulder stabilization device to function as a sling.

BRIEF DESCRIPTION OF THE DRAWINGS

A more complete understanding of the system of the present invention may be obtained by reference to the following Detailed Description when taken in conjunction with the accompanying Drawings wherein:

FIG. 1C is a front view of the elements of a shoulder stabilizer system in accordance with a preferred embodiment of the present invention;

DETAILED DESCRIPTION OF THE INVENTION

Figure 1B:
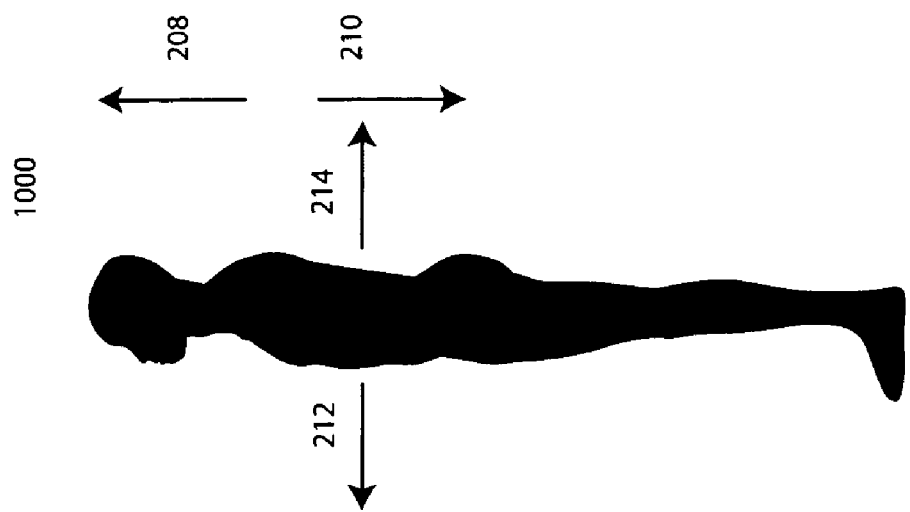
FIG. 1B is a side view of a human body in standard anatomical position.

Reference is now made in detail to the exemplary embodiments of the present invention, examples of which are illustrated in the accompanying drawings. Wherever possible, the same reference numerals are used throughout the drawings to refer to the same or similar parts.

Figure 1A:
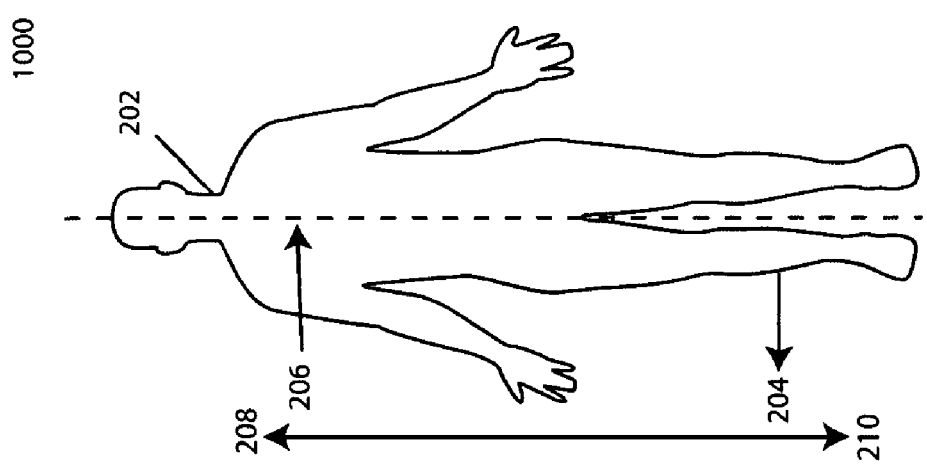
FIG. 1A is a front view of a human body in standard anatomical position.

Referring first to FIGS. 1A and 1B, any references to bodily position or direction will be made with respect to the body 1000 being in the standard anatomical position as illustrated in FIGS. 1A and 1B. References to the position of the device of the present invention with respect to the body 1000 of the wearer, as well as references to movement of the body will be made using standard terms to describe anatomical positions and movements. Each of these terms are common and well-known in the art, but are defined here for purposes of clarity. The term superior describes a direction closer to the head of the wearer, as illustrated by arrow 208 in FIGS. 1A and 1B. Likewise, the term inferior describes a direction farther from the head of the wearer, as illustrated by arrow 210. The term medial describes a direction closer to the midline 202 of the body 1000, as shown by arrow 206, while the term lateral describes a direction farther from the midline 202, as shown by arrow 204. The term anterior describes a direction toward the front of the body 1000 as shown by arrow 212, and the term posterior describes a direction toward the back of the body 1000 as shown by arrow 214. When describing bodily movements, the term abduction describes motion away from midline 202 of the body 1000, and the term adduction describes motion toward midline 202. Similarly, the term flexion refers to motion that reduces a joint angle, while extension refers to a motion that increases a joint angle.

Referring now to FIG. 1C, there is shown a preferred embodiment of a shoulder stabilizer system 100 of the present invention. The shoulder stabilizer system 100 comprises a shoulder stabilizer 10, two straps, 118 and 124, and two double sided fastener squares 138. While only two straps are shown in FIG. 1C, it will be understood to one of ordinary skill in the art that any number of straps may be used without departing from the spirit and scope of the present invention. According to an exemplary embodiment, the shoulder stabilizer 10 is constructed using approximately ⅛ inch thick perforated VeLPlush™ Neoprene on an inside 136, which provides softness and elasticity. According to another exemplary embodiment, the shoulder stabilizer 10 can be constructed using VeLPlush™ Neoprene having a thickness between ⅛ to 3/16 inch. The outside 137, comprising an anterior side 130 and a posterior side 134, is constructed of UBL, which is standard and well known in the art. The body of straps 118 and 124, with the exception of fasteners 122 and 128 may also be constructed of any appropriate material, but most preferably are also constructed using perforated VeLPlush™ Neoprene on the inside (the opposite side, not explicitly shown). Perforations within the VeLPlush™ Neoprene material allow for improved softness, comfort, and ventilation while the shoulder stabilizer system 100 of the present invention is in operation.

In all embodiments of the present invention, all fasteners may be made from any appropriate material. However, fasteners are most preferably constructed of Velcro®, available from The Velcro Company of Manchester, N.H. In various embodiments of the present invention, the entire outside of the shoulder stabilizer 10, consisting of both the posterior side 134 and the anterior side 130, except for straps and fasteners, are Velcro® compatible. The inside 136 of the shoulder stabilizer 10 is also Velcro® compatible.

Still referring to FIG. 1C, the shoulder stabilizer 10 includes a torso region 104 and a sleeve 133. The sleeve further comprises a shoulder region 132, and an upper arm region 102. According to an exemplary embodiment, the shoulder stabilizer 10 as shown in FIG. 1C is oriented to be worn on a user's right shoulder. Since the posterior side 134 is substantially identical and symmetrical to the anterior side 130, the shoulder stabilizer 10 of this preferred embodiment may also be worn on a user's left shoulder with equal effectiveness. Further, in various embodiments of the present invention, a shoulder stabilizer 10 may be worn on each shoulder in order to provide stabilization and support to both shoulders simultaneously.

Still referring to FIG. 1C, there is shown a torso fastener 106 attached to the posterior side 134 in the lower portion of the torso region 104, on the side opposite the sleeve 133. Focusing now on the upper arm region 102, there is shown an upper arm fastener 112 and a bicep fastener 114 which originate from the posterior side 134 of the upper arm region 102. Two hook straps 110 (one shown) originate from the same location as the upper arm fastener 112 and the bicep fastener 114. Each one of the two hook strap 110 includes a fastener 108 on the end of each hook strap 110.

Still referring to FIG. 1C, two straps, 118 and 124, are shown of different lengths. It will be understood to one skilled in the art that the straps used in conjunction with the present invention may be of sizes and proportions other than what is shown with respect to this preferred embodiment. As depicted, strap 118 includes a fastener 122 on each end. Likewise, strap 124 includes a fastener 128 on each end. Straps 118 and 124 enable the customization of the shoulder stabilizer 10 to the desired limitations of an individual user or medical professional, thereby providing precision control of the user's shoulder movements. Such control allows shoulder stabilizer 10 to be useful in the treatment of a wide array of shoulder injuries and ailments. Also shown are double sided fastener squares 138 which are fasteners on each side and attachable in any location on the shoulder stabilizer 10. Straps 118 and 124 and double sided fastener squares 138 will be discussed further with reference to FIGS. 2-5.

Figure 2:
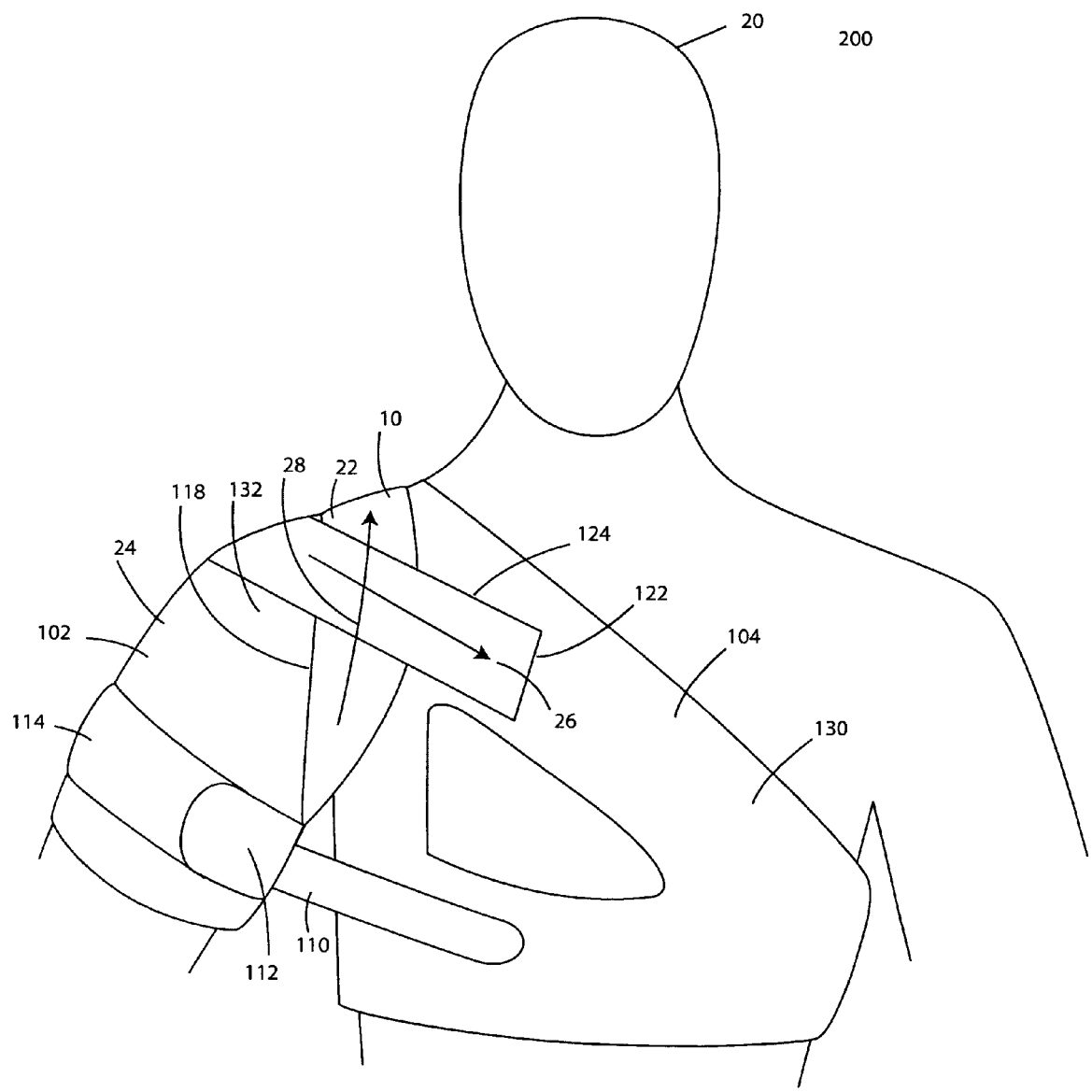
FIG. 2 is a front view of an exemplary configuration for the shoulder stabilizer system in accordance with an embodiment of the present invention.

Referring now to FIGS. 1C and 2 together, in FIG. 2 the shoulder stabilizer system 100 is shown on a user 20, according to an exemplary configuration 200. The torso fastener 106 secures the shoulder stabilizer to itself around the user 20. The shoulder stabilizer 10 is worn by inserting an upper arm 24 into the shoulder region 132 and through the upper arm region 102. Torso region 104 is then stretched tight while the stabilizer torso fastener 106 is wrapped around, and stretched medially across the anterior side 130. In this manner, the torso fastener 106 serves to attach the posterior side 134 of the torso region 104 to its anterior side 130. As the torso fastener 106 stretches medially across anterior side 130, the posterior side 134 increasingly overlaps the anterior side 130. Correspondingly, the torso region 104 of the shoulder stabilizer 10 becomes increasingly tight on the user 20. This method of securing the torso region 104 around the user 20 makes the shoulder stabilizer 10 extremely adaptable to large torsos, particularly female users with large bust sizes.

In similar fashion, upper arm fastener 112 is used for securing the upper arm region 102 around the upper arm 24. Upper arm region 102 is stretched tight around the upper arm 24 as the upper arm fastener 112 is wrapped under the inferior aspect of upper arm 24, and stretched over the anterior side 130 of the upper arm region 102. In this manner, the upper arm fastener 112 serves to attach the anterior side 130 of the upper arm region 102 with its posterior side 134. As the upper arm fastener 112 stretches further in the superior direction, the posterior side 134 of the upper arm region 102 increasingly overlaps the anterior side 130. The bicep fastener 114 functions to further secure the upper arm 24. In the embodiment of FIGS. 1 and 2, the bicep fastener 114 is wrapped in the opposite direction than the upper arm fastener 112. Bicep fastener 114 is wrapped across the posterior side 134, over the superior aspect of upper arm 24, and around to the anterior side 130 of the upper arm region 102. The use of the upper arm fastener 112 and the bicep fastener 114, allows the shoulder stabilizer 10 to be adaptable to a wide range of bicep sizes.

Still referring to FIGS. 1C and 2, hook straps 110 operate to restrict the lateral movement, also called abduction, of the arm relative to the torso of the user 20. Towards that end, the upper arm region 102 is abducted out away from the torso region 104 until the desired limit on lateral arm movement is reached. The first hook strap 110 is then stretched medially across the anterior side 130 of the torso region 104 and attached. Similarly, the second hook strap 110 (not explicitly shown), which originates from the same location, is stretched medially across the posterior side 134 of the torso region 104 and attached. In this manner, shoulder stabilizer 10 serves to restrict abduction, and any other lateral movements, of the affected shoulder of the user 20.

By way of example, various embodiments of the shoulder stabilizer system 100 may be utilized to treat acromioclavicular (AC) separation, particularly grade I and grade II AC separation, and may also be utilized in post-surgery grade III AC separation. As is known in the art, there are six grades of AC separations, with each successive grade becoming incrementally more severe. Grade I separation involves trauma to the ligaments that form the acromioclavicular joint but no severe tearing or fracturing. Grade II separation involves complete tearing of the acromioclavicular ligament, but only a sprain or partial tear of the coracoclavicular ligaments. Grade III separation involves the complete tearing of the ligaments at the AC joint, and those under the scapula that hold the shoulder in place. Grades I and II AC separation are treated without surgery, typically with rest and non-use of the injured shoulder. Grade III separations are typically treated with surgery, but may sometimes be treated with non-surgical treatments similar to the treatments of grade I and grade II separations. The shoulder stabilizer system 100 is adapted to be highly beneficial in treating grade I and grade II AC separations as well as pre-surgery and post-surgery grade III AC separations. It should be noted that the shoulder stabilizer system 100 has numerous other applications, including but not limited to, using the stabilizer to impose limitations on movement while the user is participating in athletic activities.

Figure 3:
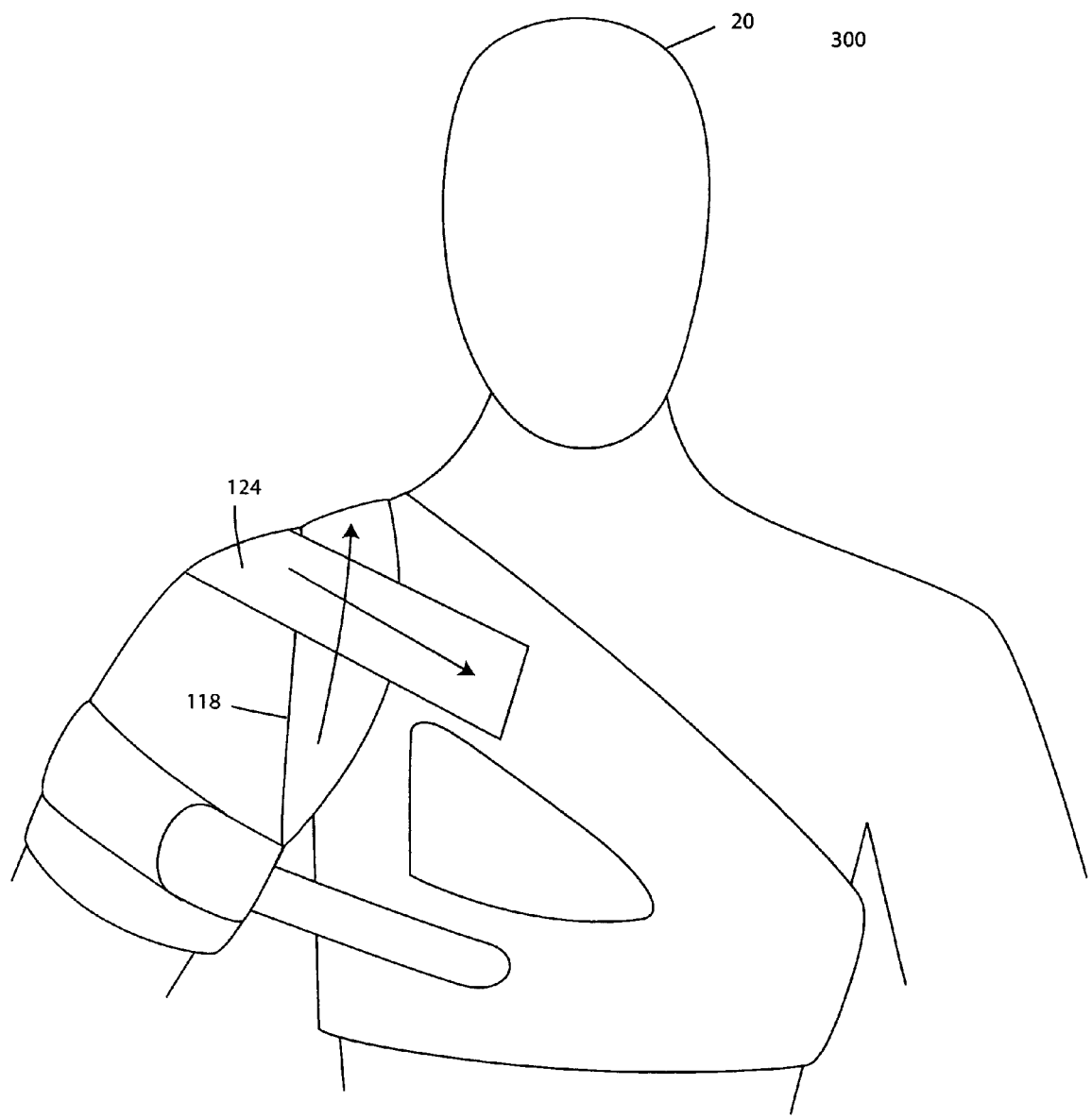
FIG. 3 is a front view of an exemplary configuration for the shoulder stabilizer system in accordance with an alternate embodiment of the present invention.

FIGS. 2-5 illustrate, by way of example, various exemplary configurations 200, 300, 400, 500 of the shoulder stabilizer system 100. Referring again to FIG. 2, there is shown an exemplary configuration 200 of the shoulder stabilizer system 100 utilizing straps 118 and 124 in operation on a user 20. An end of strap 118 is attached below the inferior aspect of upper arm 24 of the user 20 via fastener 122. Strap 118 then is wrapped over the anterior and superior aspects of the shoulder 22 in the direction of arrow 28. Strap 118 is stretched and attached to the posterior side 134 of shoulder stabilizer 10. In similar fashion, strap 124 is attached, via a fastener 128, to the anterior side 130 of the torso region 104 slightly medial of shoulder 22. Strap 124 is wrapped laterally towards the shoulder 22 in the direction of arrow 26, crossing diagonally over strap 118, stretched to the desired degree of tightness, and secured to the posterior side 134 of the shoulder stabilizer 10 via the second fastener 128. In this manner, the positioning of straps 118 and 124 help prevent and limit subluxation caused by hyperextension. Again by way of example, configuration 200 is particularly useful in treating grades I, II and III AC separations. During rehabilitation, increased amounts of movement may be desirable. FIG. 3 illustrates another similar, yet distinct, exemplary configuration 300 with strap 124 oriented slightly counterclockwise from its orientation in FIG. 2.

Figure 4:
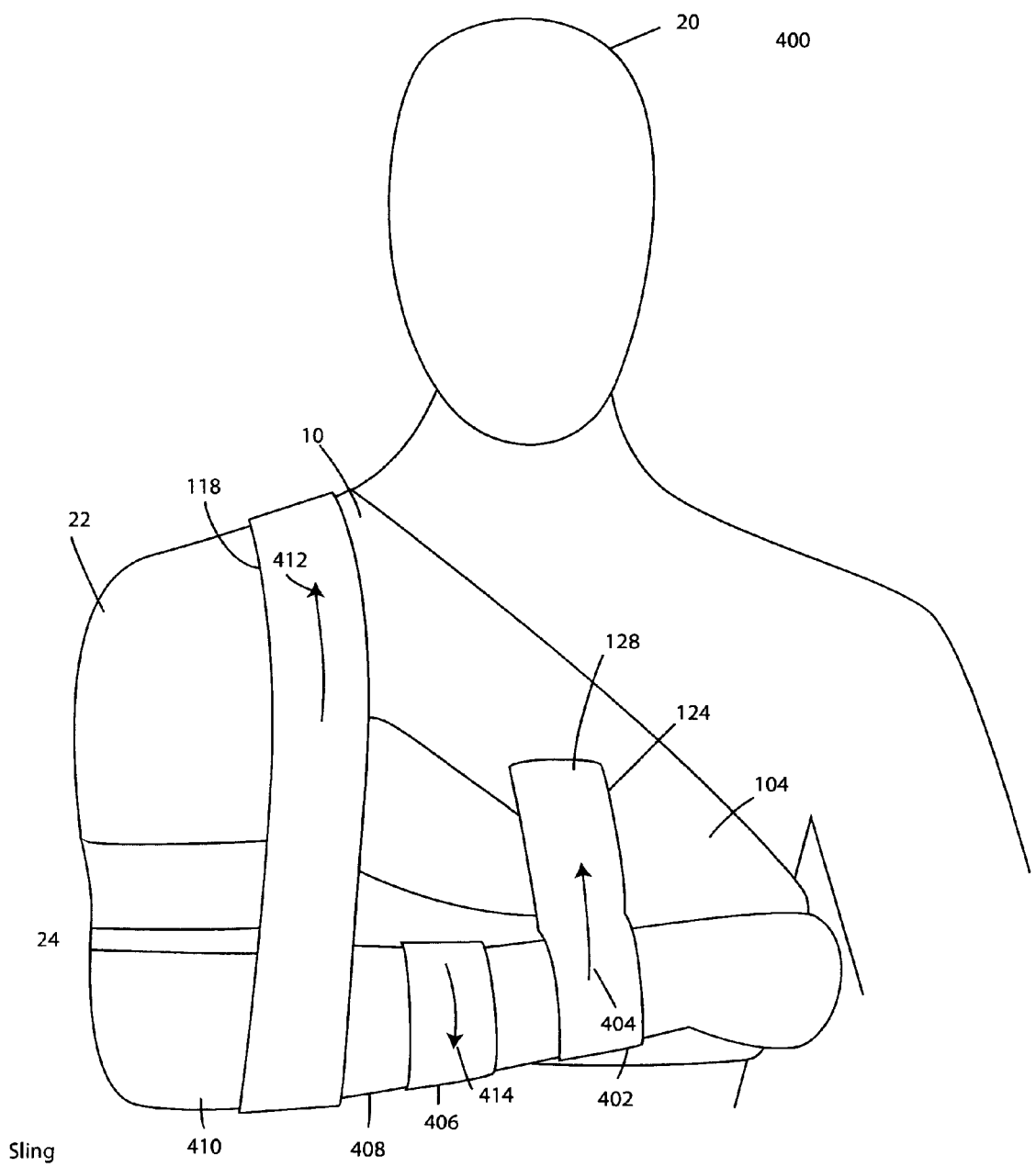
FIG. 4 is a front view of an exemplary configuration for the shoulder stabilizer system in accordance with another alternate embodiment of the present invention.

Referring now to FIG. 4, straps 118 and 124 are shown in an exemplary configuration 400 which utilizes the shoulder stabilizer system 100 to stabilize the shoulder 22 and to provide an additional function of acting as a sling. An elbow 410 is flexed to a desired elevation, shown here to be less than a 90 degree angle relative to the upper arm 24. Strap 124 is shown attached to the torso region of shoulder stabilizer 10 via a fastener 128, and wrapped downward, in the direction of arrow 404, under the inferior aspect of wrist 402, then back up and over the superior aspect of a mid-forearm 406 in the direction of arrow 414, stretched tight, and attached to the torso region of the shoulder stabilizer 10. Strap 118 completes the sling configuration by attaching a fastener 122 at a point on the medial side of an upper forearm 408 (not explicitly shown), wrapping the strap under the inferior and over the anterior aspects of the upper forearm 408, and then wrapping the strap 118 upwards over the shoulder 22 in the direction of arrow 412. The strap 118 is stretched tight and attached to the posterior side 134 of the torso region 104. In configuration 400, the arm and shoulder are stabilized with the elbow 410 elevated, which gives the shoulder stabilizer another treatment application to AC separations, as well as any other injuries which benefit from the placement of an arm in a sling. As a further advantage of this exemplary embodiment, the sling is easily adjustable by detaching the fastener 128 depicted in FIG. 4, moving the strap 124 superiorly or inferiorly, and reattaching. Strap 118 is similarly adjustable. The use of Velcro® in many preferred embodiments further facilitates and simplifies the adjustment process.

Figure 5:
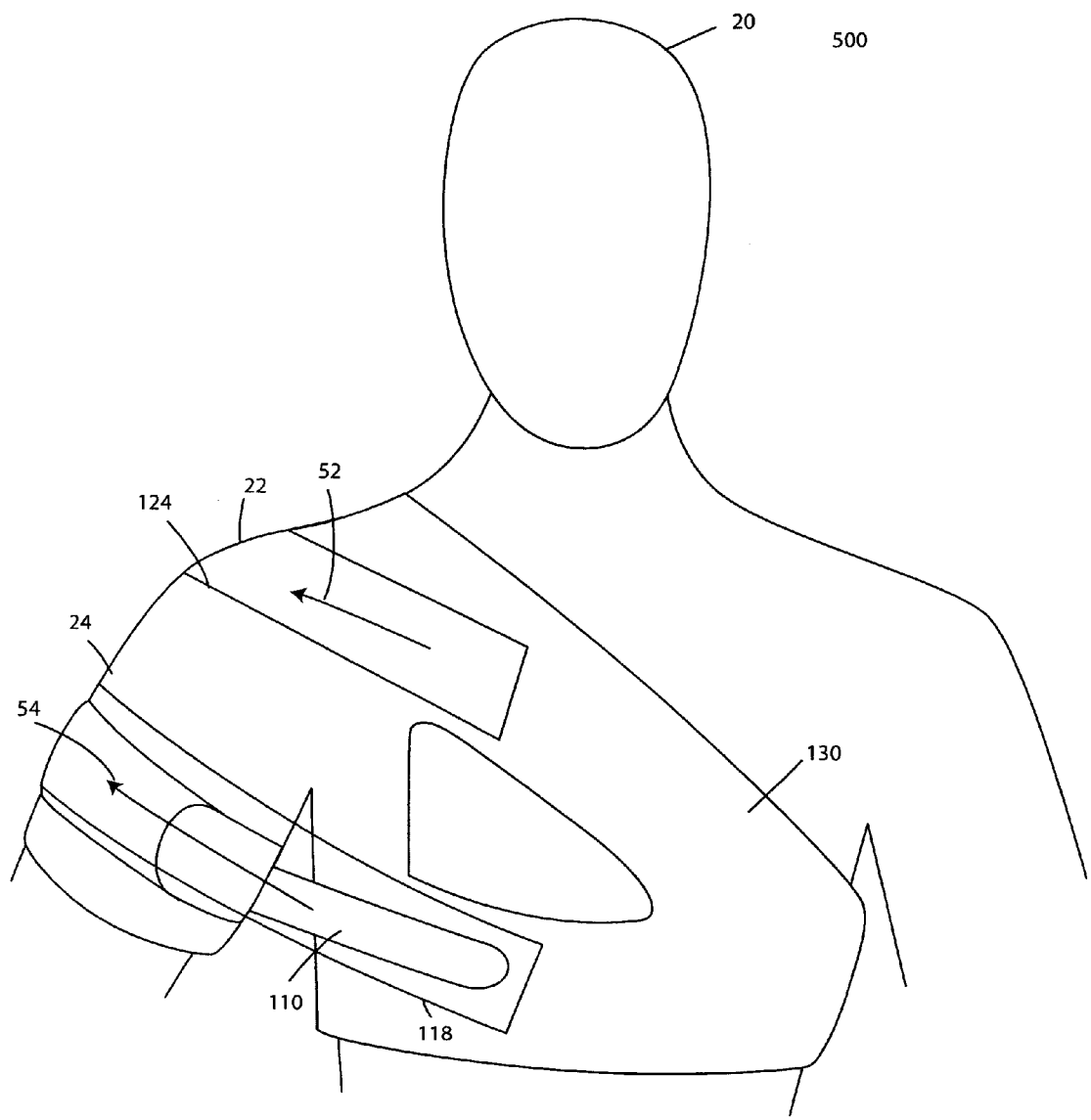
FIG. 5 is a front view of an exemplary configuration for the shoulder stabilizer system in accordance with yet another alternate embodiment of the present invention.

Referring now to FIG. 5, there is shown, by way of example, another exemplary configuration 500 for the shoulder stabilizer system 100. As a further example of the adjustability of shoulder stabilizer system 100, FIG. 5 provides an exemplary configuration 500 useful in treating injured ribs, biceps, and triceps before and after surgery. Strap 124 is shown attached to the medial torso region 104 of the anterior side 130 and stretched laterally over shoulder 22 in the direction of arrow 52. Hook strap 110 is shown attached in the manner described with respect to FIG. 1. Strap 118 is attached over hook strap 110 around the upper arm 24 in the direction of arrow 54 and over and past the second hook strap 110 on the posterior side 134 of the torso region 104. The strap 118 is then stretched tight and attached. Attached and wrapped in this way, strap 118 creates a layering effect that further strengthens limitations on arm movement.

Referring to FIGS. 1C-5 together, the function of double sided fastener squares 138 will now be discussed. Double sided fastener squares 138 may be attached at any location on the shoulder stabilizer 10. Since they are double sided fasteners, either side may be attached. With the fasteners, a user 20, or a medical professional working on behalf of the user 20, may use the double sided fasteners 138 to mark optimal positioning of straps 118 and 124 of the shoulder stabilizer system 100. Since the shoulder and body structure of users vary, the shoulder stabilizer system 100 permits the use of the shoulder stabilizer 10 to vary with the structures. As a result, straps 118 and 124 are repeatably positionable anywhere on the shoulder stabilizer 10.

Figure 6:
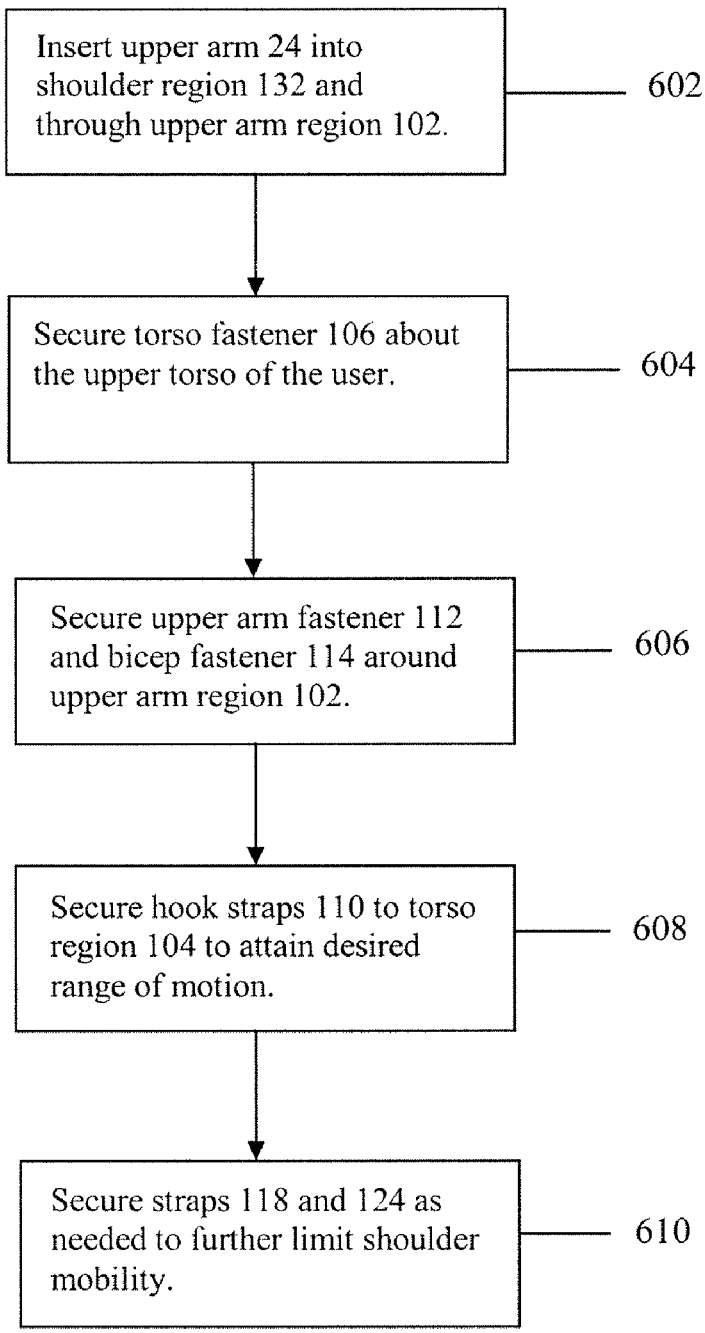
FIG. 6 is a flow diagram illustrating a method for using the shoulder stabilizer system in accordance with an embodiment of the present invention.

Referring now to FIG. 6, there is shown a flow diagram illustrating a method 600 for using shoulder stabilizer 10 according to an embodiment of the present invention. In step 602, the user inserts the upper arm 24 of the affected shoulder into the shoulder region 132 and through the upper arm region 102 of the shoulder stabilizer system 100. In step 604, torso fastener 106 is secured about the upper torso of the user. In step 606, upper arm fastener 112 and bicep fastener 114 are secured around the upper arm region 102. In step 608, hook straps 110 are secured to torso region 104 to attain the desired level of shoulder motion. In step 610, straps 118 and 124 are applied as needed to further limit shoulder mobility.

Although various embodiments of the method and apparatus of the present invention have been illustrated in the accompanying Drawings and described in the foregoing Detailed Description, it will be understood that the invention is not limited to the embodiments disclosed, but is capable of numerous rearrangements, modifications, and substitutions without departing from the spirit and scope of the invention as set forth in the foregoing specification and following claims.

What is claimed is:

1. An orthopedic stabilization device for use on a shoulder of a wearer for shoulder stabilization, the device comprising:
   a torso portion having a closed end side and an open end side, the torso portion adapted to be secured around an upper torso of the wearer;
   a sleeve, disposed on the torso closed end side, the sleeve adapted to be secured around a shoulder and an upper arm of the wearer;
   a first plurality of straps, fixed at their proximal end to a posterior aspect of the sleeve, the first plurality of straps having a first plurality of fasteners disposed at their distal end;
   wherein the first plurality of straps, upon being stretched medially across the torso portion, are operable to restrict lateral movement of the upper arm relative to the upper torso of the wearer; and
   a second plurality of straps having a second plurality of fasteners disposed at each end, whereby customizable restriction of shoulder movement may be attained by securing the first and second plurality of straps to the torso portion at various positions.

2. The device of claim 1, wherein the first and second plurality of fasteners comprise Velcro®.

3. The device of claim 1, wherein the torso portion further comprises an adjustable fastener disposed along the open end side.

4. The device of claim 3, wherein the adjustable fastener comprises Velcro®.

5. The device of claim 1, wherein the sleeve further comprises a third plurality of fasteners adapted to secure the sleeve about the upper arm of the wearer.

6. The device of claim 5, wherein the third plurality of fasteners comprises Velcro®.

7. The device of claim 1, wherein the torso portion and the sleeve comprise neoprene.

8. The device of claim 1, wherein the first plurality of straps are adapted to limit abduction of an arm of the wearer.

9. The device of claim 1, wherein the second plurality of straps are adapted for use as a sling.

10. The device of claim 1, wherein the device is adapted for treatment of acromioclavicular separation.

11. The device of claim 1, wherein the device is adapted for treatment of biceps injuries.

12. The device of claim 1, wherein the device is adapted for treatment of triceps injuries.

13. The device of claim 1, wherein the device is adapted for treatment of rib injuries.

14. A method for stabilizing a shoulder of a wearer of the type used in an orthopedic treatment, the method comprising:
   providing a shoulder stabilization device having a sleeve and a torso portion adapted to receive an arm of the wearer;
   inserting the arm of the wearer through the sleeve of the shoulder stabilization device;
   securing the torso portion around an upper torso of the wearer;
   securing the sleeve around an upper arm and shoulder of the wearer;
   stretching a first plurality of straps medially across the torso portion so as to restrict lateral movement of the upper arm relative to the upper torso of the wearer, wherein the first plurality of straps being fixed at their proximal end to a posterior aspect of the sleeve; and
   selectively applying at least one strap of a second plurality of straps to further restrict the shoulder to a desired range of motion, whereby the selective application of the second plurality of straps allows customization of the shoulder stabilization device.

15. The method of claim 14, wherein the torso portion comprises an adjustable fastener disposed along an open end side.

16. The method of claim 14, wherein the sleeve further comprises a third plurality of fasteners adapted to secure the sleeve about the upper arm of the wearer.

17. The method of claim 14, wherein the second plurality of straps are applied in such a way to function as a sling.

18. The method of claim 14, wherein the second plurality are applied in such a way to further limit lateral movement of the shoulder of the user.

19. The method of claim 14, wherein the device is adapted for treatment of acromioclavicular separation.

20. A method of stabilizing a shoulder of a wearer of the type used in orthopedic treatment, the method comprising:
   providing a shoulder stabilization device having a sleeve and a torso portion adapted to receive an arm of the wearer, the sleeve having a plurality of straps fixed thereto;
   inserting the arm of the wearer through the sleeve;
   securing the torso portion around an upper torso of the wearer;
   securing the sleeve around an upper arm and shoulder of the wearer;
   stretching the plurality of straps, fixed to the sleeve, medially across the torso portion so as to restrict lateral movement of the upper arm relative to the upper torso of the wearer;
   applying a first strap, having a fastener disposed at each end, so as to support a wrist and hand of the user; and
   applying a second strap, having a fastener disposed at each end, so as to support an elbow and lower arm of the user, whereby the application of the first and second straps enables the shoulder stabilization device to function as a sling.

* * * * *